United States Patent [19]
Gassman et al.

[11] 3,960,926
[45] June 1, 1976

[54] PROCESS FOR PREPARING AZASULFONIUM HALIDE SALTS

[75] Inventors: Paul G. Gassman; Gordon D. Gruetzmacher, both of Columbus, Ohio

[73] Assignee: The Ohio State University Research Foundation, Columbus, Ohio

[22] Filed: Apr. 30, 1975

[21] Appl. No.: 573,059

Related U.S. Application Data

[62] Division of Ser. No. 429,050, Dec. 28, 1973.

[52] U.S. Cl............................ 260/470; 260/294.8 D; 260/294.8 E; 260/294.8 G; 260/551 S
[51] Int. Cl.$^2$........................................ C07C 145/02
[58] Field of Search................. 260/551 S, 294.8 D, 260/294.8 E, 294.8 G

*Primary Examiner*—Lewis Gotts
*Assistant Examiner*—S. P. Williams
*Attorney, Agent, or Firm*—Gordon W. Hueschen

[57] ABSTRACT

Preparing azasulfonium halide salt derivatives of an aniline by reacting a halogen with a non-carbonylic dihydrocarbon sulfide, a beta-carbonylic hydrocarbon sulfide, or a β-thio ester or amide to form a halogen:sulfur compound complex and then reacting the complex with an aniline to form the azasulfonium halide salts. The azasulfonium halide salts are useful as intermediates in processes for making ortho-alkylated anilines, indoles, and 2-oxindoles which have a variety of known uses.

19 Claims, No Drawings

PROCESS FOR PREPARING AZASULFONIUM HALIDE SALTS

The invention described herein was made in the course of work done under a grant or award from the United States Department of Health, Education and Welfare.

This is a division of application Ser. No. 429,050, filed Dec. 28, 1973.

FIELD OF THE INVENTION

This invention relates to the production of azasulfonium halide salts which are particularly useful in processes for making ortho-alkylated anilines, indoles and 2-oxindoles. The process of this invention is particularly advantageous in processes which involve or require the use of the less stable or more reactive substituted anilines such as methoxy-substituted anilines, but the new process improvement of this invention is not limited thereto.

BACKGROUND OF THE INVENTION

In U.S. application for Pat. Ser. No. 327,294, filed Jan. 29, 1973, now U.S. Pat. No. 3,894,034 there is described and claimed a process for ortho-alkylating a primary or secondary aromatic amine involving chemical steps comprising reacting an N-halo-aromatic amine with an organic thio-ether to form an azasulfonium salt, reacting the azasulfonium salt with a base to form an ortho-hydrocarbon-S-hydrocarbon aromatic amine thio-ether. If desired, the thio-ether product can be reduced to an ortho-hydrocarbon aromatic amine. This reaction is applicable to both anilines and aminopyridines.

The disclosure of that application and the prior art referred to therein are incorporated herein by reference thereto.

In U.S. application for Pat. Ser. No. 355,198, filed Apr. 27, 1973, now U.S. Pat. No. 3,901,899 there is described and claimed a process for preparing indoles by reacting an N-haloaniline with a β-carbonyl hydrocarbon-S-hydrocarbon sulfide, or an acetal or ketal form thereof, to form an azasulfonium halide salt, and then treating the azasulfonium halide salt with a base to form a thio-ether substituted indole or thio-ether substituted indolenine if a β-carbonyl sulfide or α-alkyl-β-carbonyl sulfide had been used, respectively, or with a base and then with an acid if a β-carbonyl sulfide acetal or ketal had been used, to form the thio-ether-substituted indole or thio-ether substituted indolenine. Thereafter if desired, the thio-ether indole or thio-ether indolenine can be reduced, e.g., with Raney nickel, to remove the thio-ether group from the indole. The process is applicable to both anilines and aminopyridines.

The disclosure of that application and the prior art referred to therein is incorporated herein by reference thereto.

In the U.S. application Ser. No. 355,207, filed Apr. 27, 1973, now U.S. Pat. No. 3,897,451 there is described and claimed a process for preparing 2-oxindole compounds by reacting an N-haloaniline with a β-thiocarboxylic ester or amide to form an azasulfonium halide salt, treating the azasulfonium halide salt with a base to form an ortho-[1-(thio-ether) (hydrocarbonoxycarbonyl)alkyl]aniline or an ortho-[1-(thio-ether) (aminocarbonyl)alkyl]aniline, and then treating the ortho-substituted aniline with an acid to form a 3-thio-ether-2-oxindole compound. Thereafter, if desired, the 3-thio-ether-2-oxindole can be reduced, e.g., with Raney nickel, to remove the thio-ether group and to form the 2-oxindole.

The disclosure of that application and the prior art referred to therein is incorporated herein by reference thereto.

In the above referenced processes for preparing each of the ortho-alkylated anilines, the indoles, and 2-oxindoles, the azasulfonium halide salt formation step is a common requirement of each process. In continued studies of the above processes it was found that for the preparation of some compounds however, the above process has some limitations. The limitations are associated with the stability of some N-haloanilines when there was present a cation stabilizing group substituent on the aniline ring, e.g. p-methoxyl. The N-chloro-p-anisidines are extremely reactive, even at temperatures as low as −78°C. When using such materials in the above referenced processes to synthesize 4-methoxyanilines, 5-methoxyindoles or 5-methoxy 2-oxindoles respectively, the reactions were difficult to control for the purpose of getting practical yields. Thus, in the development of these chemical processes to practical use in possible commercial operations, there is a need for an alternative process for preparing azasulfonium halide salt intermediates, which process improvement would be particularly useful where highly reactive anilines are to be used.

OBJECTS OF THE INVENTION

It is an object of this invention to provide an alternative process for preparing azasulfonium halide salt derivatives of anilines.

It is a further object of this invention to provide an improvement in processes for preparing ortho-alkylated anilines, indoles and 2-oxindoles from aniline starting materials.

It is also an object of this invention to provide azasulfonium halide salts by a process which involves the nucleophilic attack of anilines on halogen:sulfide compound complexes.

Other objects, aspects and advantages of this invention will become apparent to those persons skilled in this art from the specification and claims which follow.

SUMMARY OF THE INVENTION

Briefly, by this invention it has been discovered that azasulfonium halide salt derivatives of anilines can be prepared by (a) reacting elemental halogen with an organic sulfide compound to form a halogen:sulfide compound complex and (b) reacting the aniline with the halogen:sulfide compound complex to form the azasulfonium halide salt. The reactions are conducted under mild, substantially anhydrous, low temperature conditions in an organic liquid diluent which will dissolve at least a portion of the reactants. Thereafter the azasulfonium halide salt is treated with base, or with base and then with acid to form the respective ortho-alakylated aniline, thio-ether-substituted indole or thio-ether-substituted-2-oxindole. If desired, the thio-ether compounds can be reduced, e.g., with Raney nickel, to remove the thio-ether group and to form the respective ortho-alkylated aniline, indole, or 2-oxindole, respectively, which have a variety of known uses.

DETAILED DESCRIPTION OF THE INVENTION

The invention herein is an alternative, and in some cases, an improved, process for preparing azasulfonium halide salts. Azasulfonium halide salts can be used in processes for preparing ortho-alkylated anilines, indoles and 2-oxindoles from aniline starting materials. This invention is thus also an improvement in processes for preparing ortho-alkylated anilines, indoles and 2-oxindoles.

According to this invention there is provided a process for preparing an azasulfonium halide salt which comprises (a) reacting an elemental halogen with a sulfide compound selected from the group consisting of (I) a non-carbonylic dihydrocarbon sulfide, defined below, II (a) a beta-carbonylic hydrocarbon sulfide or (b) an acetal or ketal derivative thereof, defined below, and (III) (a) a beta-thio ester or (b) a beta-thio amide, defined below, under substantially anhydrous conditions in an organic solvent medium which is sufficiently polar to dissolve the reactants, and at a temperature low enough to control the reaction, and (b) combining and reacting an aniline with the halogen:sulfur compound complex from step (a), under essentially the same conditions as indicated above to form the azasulfonium halide intermediate.

Thus, in a process for preparing a compound selected from the group consisting of an ortho-alkylated aniline, an indole, and a 2-oxindole involving as one of the steps of that process the use of an azasulfonium halide salt derivative of an aniline, this invention provides an improvement which comprises (a) reacting an elemental halogen with the respective sulfur compound, as indicated above, to form a halogen:sulfur compound complex and (b) reacting the selected aniline with the halogen:sulfur compound complex from step (a) under substantially anhydrous conditions in an organic liquid diluent to form the azasulfonium halide intermediate.

As used herein, the term "elemental halogen" means chlorine or bromine.

When it is desired to prepare an ortho-alkylated aniline using the improvement of this invention the halogen is reacted with a non-carbonyl organic sulfide of the formula

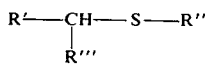    I wherein
R' is hydrogen, lower alkyl or phenyl;
R'', taken separately, is lower alkyl or phenyl;
R''', taken separately, is hydrogen, lower alkyl or phenyl; and
R'' and R''' when taken together with the

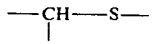

denote a ring containing 3 to 5 methylene carbon atoms, to form a halogen:sulfur compound complex, and then the selected aniline is reacted with the halogen:sulfur compound complex to form an azasulfonium salt of the formula:

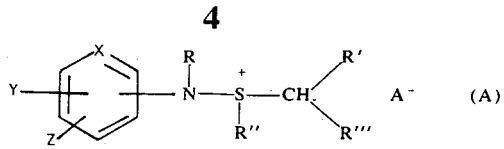

where
R', R'' and R''' are as defined above
R is hydrogen or a hydrocarbon radical free of aliphatic unsaturation containing from 1 to 8 carbon atoms;
X is —CH= or —N= and is in a position ortho, meta or para relative to the —N(R)—group on the ring
Y and Z are each hydrogen or a non-interfering substituent such as halogen (chlorine, bromine, fluorine, iodine), nitro, cyano, amino (—NH$_2$), lower alkylamino, lower alkyl, lower alkyloxy, lower acyloxy or a carbonyloxy-lower alkyl or a carbonyloxy-phenyl; and
A$^-$ denotes a halogen ion, preferably a chlorine or bromine ion. These sulfides and azasulfonium salts are described in the above referenced application Ser. No. 327,294.

As used herein the term "lower alkyl" means a $C_1$ to $C_6$-alkyl radical, e.g., methyl, ethyl, propyl, isopropyl, n-butyl, isobutyl, tert-butyl, n-pentyl, n-hexyl, and the like. The term "lower alkyloxy" denotes a $C_1$ to $C_6$-alkyl-O-group wherein the $C_1$ to $C_6$-alkyl group is exemplified as above. The term "lower acyloxy" denotes a formyloxy and a $C_1$ to

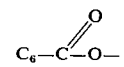

group wherein the $C_1$ to $C_6$-alkyl is exemplified as above.

The term "aniline" as used herein means a primary or secondary aniline or amino-pyridine, both being referred to herein as an "aniline." The aniline compounds which can be used in the process of this invention are those which have a free, unsubstituted position on the aromatic ring ortho to the amino group. Such compounds are known compounds, many of them being articles of commerce. Many of them are described in publications such as "Chem. Sources" Directories Publishing Co., Flemington, N.J. 08822 (1972). Definitions and examples of such anilines are also given in the above referenced application Ser. No. 327,294, 355,198 and 355,207.

When it is desired to prepare an indole using the improvement of this invention the halogen is reacted with a β-carbonyl sulfide compound or a 3-carbonyl sulfide acetal or ketal compound having a formula selected from the group consisting of

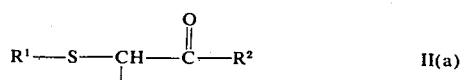    II(a)

and

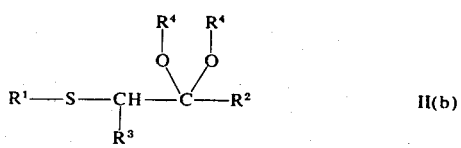    II(b)

wherein
R[1] is lower alkyl or phenyl;
R[2] is hydrogen, lower alkyl or phenyl;
R[3] is hydrogen, lower alkyl, phenyl or benzyl;
R[2] can be attached to R[3] as part of a cyclic ring system containing 5 to 8 carbon atoms;
each R[4] is lower alkyl or the two R[4] radicals are taken together with the

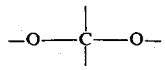

moiety to complete a cyclic ketal or acetal having from 3 to 4 carbon atoms in the ring,
to form a halogen:sulfur compound complex, and then the selected aniline is reacted with the halogen:sulfur complex to form an azasulfonium salt having a formula selected from the group consisting of

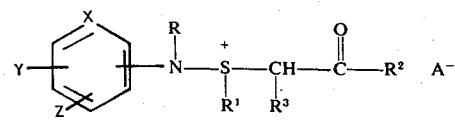

and

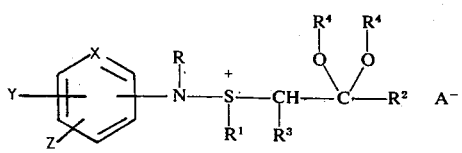

wherein X, Y, Z, R, R[1], R[2], R[3], each R and A[−] are as defined above. These azasulfonium halide salt compounds of structure (B) and (C) are then treated as indicated above and as exemplified in the above-referenced application Ser. No. 355,198, as intermediates in the synthesis of indole compounds. These sulfides and azasulfonium salts are described in the above-referenced application, Ser. No. 355,198.

When it is desired to prepare a 2-oxindole, the halogen is reacted with a β-thio carboxylic ester (IIIa) or a β-thio carboxylic amide (IIIb) having a formula selected from the group consisting of

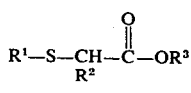

and

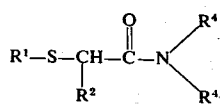

wherein
R[1] is lower alkyl, phenyl or benzyl;
R[2] is hydrogen, lower alkyl, phenyl or benzyl;
R[3] is lower alkyl, phenyl or benzyl;
each R[4] is hydrogen or lower alkyl, or the two R[4] groups are taken together with the nitrogen to form a ring containing from 4 to 5 methylene carbon atoms and up to one ring oxygen atom,
to form a halogen:sulfur compound complex, and then the selected aniline is reacted with the halogen:sulfur compound complex to form an azasulfonium halide salt having a formula selected from the group consisting of

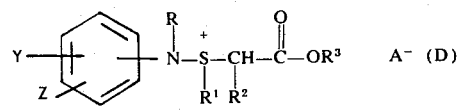

and

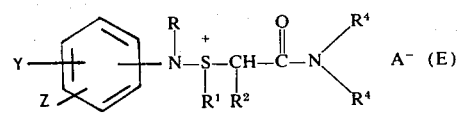

wherein Y, Z, R, R[1], R[2], R[3], each R and A[−] are as defined above. These sulfides of formulas III(a) and (b) and the azasulfonium halide salt compounds of structures (D) and (E) are then treated as indicated above and as exemplified in the above-referenced application Ser. No. 355,207 as intermediates in the synthesis of 2-oxindole compounds.

In the first step (a) of the process of this invention the reaction of the halogen with the sulfide compound produces a halogen:sulfur compound complex which can be illustrated by the formula

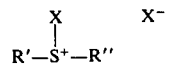

where, in this structure, R' and R'' denote the residue of the sulfide starting materials as defined above, and X denotes halogen, preferably chlorine or bromine. This complex is written here in the form of a salt, although we are not yet sure that the complex is a salt, and we do not wish to be bound by that theory. However, this structure does account for the material balance and the nature of the chemical attack by the aniline on the complex in the following step of the process, regardless of the definitions of the R' and R'' radicals, as illustrated above, at this stage of the process.

Examples of organic sulfide compounds which can be reacted with the halogen to form the halogen:sulfur compound complex are listed in the above referenced applications for Pat. Ser. Nos. 327,294, 355,198 and 355,207, and illustrative examples of each type are given below in the detailed Examples.

In the second step (b) of the process of this invention the aniline is commingled with the halogen:sulfur compound complex to effect reaction between the aniline to form the azasulfonium halide salt intermediates, as described above. It is believed that the reaction involves nucleophilic attack of the aniline on the complex to form the azasulfonium halide salt. The azasulfonium salt aniline derivatives can be recovered, if desired, but more often it is preferred to prepare and use them in situ without a separate recovery step.

In conducting the process of this invention the halogen and sulfur compounds are combined under substantially anhydrous conditions in an organic diluent or solvent, at a temperature ranging from the Dry-Ice/acetone mixture temperatures (about −78°C) to about 0°C for a time sufficient to effect complex formation. A wide variety of organic diluents or solvents can be used. Solvents or diluents as extreme in polarity as toluene and methanol can be used. Methylene chloride has been most commonly used in our work, but solvents such as tetrahydrofuran, chloroform, acetonitrile, petroleumether and mixtures of organic liquids such as methylene chloride/acetonitrile and the like can also be used.

The halogen:sulfur compound complex reaction step is usually quite rapid, but the mixture containing the halogen, the sulfur compound and any solvent or diluent is usually stirred for a time sufficient to insure complete reaction. Then the aniline, alone or in solution in a common diluent, can be added or commingled with the solution or mixture of the halogen:sulfur compound complex. Since the reactions are in most cases exothermic in nature, the reaction mixture is preferably cooled to maintain the temperature of the contents of the reaction vessel generally below about 9°C. Temperatures can be allowed to go somewhat higher, but the yields of the final product is effected thereby and thus higher temperatures are not preferred.

When any exothermic reaction has subsided and formation of the azasulfonium halide salt appears to be as complete as optimumly possible, teh azasulfonium halide salt can be isolated and purified. However, it is preferred to directly treat the azasulfonium halide salt containing mixture with base or, with base and then with acid, to prepare the orthoalkylated aniline, the 3-thio-ether indole or 3-thio-ether-2-oxindole, as described above.

In a typical procedure, using the process improvement of this invention, on a laboratory scale, from 0.044–0.05 mol of organic sulfide in 10 ml of methylene chloride at about −70°C is added to a solution of 0.044 mol of chlorine in 120 ml of methylene chloride. On addition, a slight exotherm (about 5°C) is noted, evidencing that formation of the chlorine:sulfide compound complex is occurring. The solution of the complex is stirred for about 5 minutes and then a solution of one equivalent of the selected aniline and one equivalent of triethylamine in 10 ml of methylene chloride at about −70°C is added dropwise to form the azasulfonium halide salt aniline derivative.[1]

The solution of the azasulfonium halide salt is stirred for 2 to 4 hours at cold temperatures (preferably about −70°C) and 0.05 mol of sodium methoxide in 15 ml of absolute methanol is added.[2]

The cooling bath is removed and the reaction mixture is allowed to warm to room temperature with stirring over a 12 hour period. Work-up of the reaction mixture by dilution with water and extraction with methylene chloride gives the crude ortho substituted aniline. When the sulfide contains a β-keto function, spontaneous cyclization to produce indoles occurs. When the sulfur in the sulfide compound is beta to a carboalkoxy group, acid is added to catalyze cyclization to 2-oxindole.

Footnotes:
1—The triethylamine is used to neutralize the hydrochloric acid which is generated. In place of the aniline-triethylamine mixture, two equivalents of the aniline can be used in some cases.
2—In the indole and oxindole synthesis, triethylamine (neat) is used as the base in the ylid generation step, and the reaction mixture is stirred for 15 minutes at −70°C and allowed to warm to room temperature.

Through this general procedure p-anisidine could be converted into 4-methoxy-2-(methylthiomethyl)aniline in 62 percent yield. The procedure is quite general. For a series of anilines (toluidine, aniline, p-chloroaniline, 4-nitroaniline, and p-ethoxycarbonylaniline) reaction of the aniline with the chlorine:sulfur compound complex chlorodimethylsulfonium chloride through the azasulfonium halide salt gave the corresponding 2-(methylthiomethyl)anilines in 54, 67, 45, 31 and 35% yields, respectively. The reaction is not restricted to chlorodialkylsulfonium chlorides. For example, when bromodimethylsulfonium bromide was used with aniline to form the azasulfonium bromide salt of aniline a 69 percent yield of 2-(methylthiomethyl)aniline was obtained. Treatment of aniline with halotetramethylenesulfonium halide (chloride or bromide) to form the azasulfonium salt followed by base treatment, gave 2-(2-tetrahydrothienyl)aniline in 20 percent yield. The use of β-keto sulfides and β-carboalkoxysulfides in this reaction provided a simple route to indoles and 2-oxindoles. Treatment of p-anisidine with chlorine:sulfur compound complex

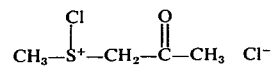

to form the azasulfonium halide salt of the anisidine, followed by triethylamine, according to the above general procedure, gave 2-methyl-5-methoxy-3-methylthioindole in 38 percent yield. The reaction is not restricted to p-anisidine. With aniline, p-chloroaniline, and benzocaine, we obtained the corresponding unsubstituted, 5-chloro- and 5-ethoxycarbonyl-2-methyl-3-methylthioindoles in 68, 45 and 33 percent yields, respectively. Raney nickel desulfurization of the 3-methylthio compound gave 5-methoxy-2-methylindole in 72 percent yield.

Similarly, treatment of p-anisidine with the halogen:sulfur compound complex

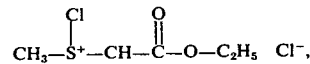

followed by treatment of the resulting azasulfonium halide salt with triethylamine and then with hydrochloric acid, gives the 5-methoxy-3-methylthio-2-oxindole in 53 percent yield. Raney nickel desulfurization of the 3-methylthio compound gave 5-methoxy-2-oxindole in 71 percent yield.

The invention is further illustrated by the following examples which are not intended as limiting the invention thereto but only as illustrating the operation, applicability and utility of the invention. In the examples, temperatures are in degrees centigrade unless indicated otherwise.

EXAMPLE 1

Preparation of 4-methoxy-2-(thiomethoxymethyl)aniline from chlorodimethylsulfonium chloride and p-anisidine.

In a graduated test tube was condensed 2.0 ml (0.044 mole) of chlorine at −78° (dry ice-acetone), 10 ml of dry methylene chloride was added to the chlorine, the solution was allowed to warm slightly, stirred with a spatula, and poured into 100 ml of dry methylene chloride at −78° and maintained under a static nitrogen pressure. The graduated test tube was washed with an additional 10 ml of methylene chloride and this was added to the reaction mixture. The temperature of the pale yellow solution was cooled to ca. −70° and 3.90 ml (0.05 mole) of dimethyl sulfide in 10 ml of dry methylene chloride was added. The exotherm was kept to less than 5°, and the yellow color had dissipated upon completion of the addition of the dimethyl sulfide solution. The solution of the resulting chlorodimethylsulfonium chloride was stirred for 5 min; a solution of 2.76 g (0.02 mole) of p-anisidine, and 2.80 ml (0.02 mole) of triethylamine in 10 ml of dry methylene chloride was added dropwise to form the azasulfonium chloride salt of p-anisidine. The resultant purple solution was stirred for 4 hours at −70°, 3.24 g (0.06 mole) of sodium methoxide in 15 ml absolute methanol was added dropwise to the reaction mixture. The cooling bath was allowed to warm to room temperature overnight (ca. 16 hr). The reaction was quenched with 150 ml of 10% aqueous sodium hydroxide; the layers separated and the aqueous phase was extracted two times with 100-ml portions of methylene chloride, the organic layers were combined, dried with anhydrous magnesium sulfate, filtered, and concentrated in vacuo to yield a dark oil. Column chromatography on silica gel (etherhexane) gave 2.24 g (0.0124 mole, bp 95°–100° (0.16 mm), 62%, ($n_D^{23.6}$ 1.5998 vs. $n_D^{23.4}$ 1.6011 for an analytical sample) of 4-methoxy-2-(thiomethoxymethyl)aniline. The infrared (ir) and nuclear magnetic resonance (nmr) spectra were identical to previously prepared samples.

EXAMPLE 2

Preparation of 2-(thiomethoxymethyl)aniline from chlorodimethylsulfonium chloride and aniline.

Chlorodimethyl sulfonium chloride was prepared as described in Example 1 for the preparation of 4-methoxy-2-(thiomethoxymethyl)aniline. A solution of 1.86 g (0.02 mole) of aniline and 2.80 ml (0.02 mole) of triethylamine in 10 ml of dry methylene chloride was added dropwise to the clear solution of chlorodimethylsulfonium chloride to form the azasulfonium chloride salt of aniline. A white precipitate formed after ca. 1 hr; the reaction mixture was stirred for 6 hours at −70°. The cooling bath was allowed to warm to room temperature overnight (ca. 16 hr). A work-up procedure identical to that used in the preparation of 4-methoxy-2-(thiomethoxymethyl)aniline gave a dark oil. This oil was refluxed in 100 ml of acetonitrile and 5 ml of triethylamine for 5 hours. The solvent was removed in vacuo; the resultant oil was chromatographed on silica gel (ether-hexane) to produce 2.04 g (0.0133 mole, bp 80°–82° (0.08 mm), 67%, $n_D^{21.8}$ 1.6094 vs. $n_D^{24.0}$ 1.6083 for a previously prepared sample) of 2-(thiomethoxymethyl)aniline. The ir and nmr spectra were identical to those of previously prepared samples.

EXAMPLE 3

Preparation of 4-methyl-2-(thiomethoxymethyl)aniline from chlorodimethylsulfonium chloride and p-toluidine.

4-Methyl-2-(thiomethoxymethyl)aniline was prepared from chlorodimethylsulfonium chloride, prepared as described in Example 1, and p-toluidine, to form the azasulfonium chloride salt, followed by base treatment, in 54 percent yield after column chromatography on silica gel (ether-hexane eluant) and distillation bp 90°–95° (0.03 mm) in a procedure identical to that used in Example 2 for the preparation of 2-(thiomethoxymethyl)aniline. The distillate, 4-methyl-2-(thiomethoxymethyl)aniline, solidified upon standing mp 45°–47° (lit[1] 42°–45°). The ir and nmr spectra were identical to previously prepared samples.

[1] P. Claus, W. Vycudilik, and W. Reider, Monatsh. Chem., 102, 1571 (1971).

EXAMPLE 4

Preparation of 4-chloro-2-(thiomethoxymethyl)aniline from chlorodimethylsulfonium chloride and 4-chloroaniline.

Chlorodimethylsulfonium chloride was prepared as described in Example 1 for the preparation of 4-methoxy-2-(thiomethoxymethyl)aniline. A solution of 2.55 g (0.02 mole) of 4-chloroaniline and 2.80 ml of triethylamine in 10 ml of dry methylene chloride was added dropwise to the clear solution of chlorodimethylsulfonium chloride to form the azasulfonium salt of 4-chloroaniline. The resultant solution was stirred for 8 hours at ca. −70°. A solution of 3.24 g (0.06 mole) of sodium methoxide in 15 ml of absolute methanol was added, the cooling bath was allowed to warm to room temperature, and the reaction mixture stirred overnight. The reaction was quenched with 100 ml of 10% aqueous sodium hydroxide; the layers were separated; the aqueous phase was washed with two 100-ml portions of methylene chloride. The combined organic phases were dried over anhydrous magnesium sulfate, filtered, and concentrated in vacuo to give a red oil. This oil was taken up in 100 ml of acetonitrile and 5 ml of triethylamine and refluxed for 18 hours. The solvents were removed in vacuo to yield a red oil which solidified upon standing. Column chromatography on silica gel (ether-hexane eluant) gave 1.68 g [0.009 mole, mp 76°–78° (anal. sample previously prepared mp 78°–80°), 45% yield] of 4-chloro-2-(thiomethoxymethyl)aniline. The ir and nmr spectra were identical to previously prepared samples.

EXAMPLE 5

Preparation of 4-nitro-2-(thiomethoxymethyl)aniline from chlorodimethylsulfonium chloride and 4-nitroaniline.

In a graduated test tube was condensed 2.0 ml (0.044 mole) of chlorine at −78° (dry ice-acetone), 10 ml of dry methylene chloride was added to the chlorine, the solution was allowed to warm slightly, stirred with a spatula, and poured into a solution of 75 ml of acetonitrile and 25 ml of methylene chloride at −50° to −40° (40% aqueous methanol-dry ice bath), and maintained under a static nitrogen pressure. The graduated test tube was washed with an additional 10 ml of methylene chloride and this was added to the solution. A solution of 3.90 ml (0.05 mole) of dimethyl sulfide in 10 ml of dry methylene chloride was added; the exotherm was kept to less than 5° by dropwise addition and the yellow color had dissipated upon completion of the addition of the dimethyl sulfide solution. This solution of the chlorodimethylsulfonium chloride was then stirred for 5 min; a solution of 2.76 g (0.02 mole) of p-nitroaniline and 2.80 ml (0.02 mole) of triethylamine in 20 ml of acetonitrile and 20 ml of methylene chloride was added dropwise, into the chorodimethylsulfonium chloride solution maintaining the temperature to −40° or less. A voluminous precipitate of the azasulfonium chloride salt of 4-nitroaniline formed and the reaction mixture was stirred for 9 hours while maintaining the temperature from −50° to −40°. A solution of 3.24 g (0.06 mole) of sodium methoxide in 15 ml of methanol was added to the azasulfonium salt reaction mixture, the cooling bath was removed, and the solution was stirred overnight. The reaction was quenched by addition of 100 ml of 10% aqueous sodium methoxide; the layers were separated, the aqueous phase was extracted two times with 100-ml portions of methylene chloride. The combined organic phases were dried over anhydrous magnesium sulfate, filtered, and concentrated in vacuo to produce a yellow solid. This solid was taken up in 150 ml of dry toluene and 5 ml of triethylamine and refluxed for 48 hours. The solvents were again removed in vacuo to yield a yellow solid. Column chromatography on silica gel (ether-hexane eluant) gave 1.24 g (0.0063 mole, mp 73°–75° (lit[1] mp 75°–77°), 31%) of 4-nitro-2-(thiomethoxymethyl)aniline. The ir and nmr spectra were identical to previously prepared samples. Also, 1.30 g (0.0094 mole, 42%) of 4-nitroaniline was recovered.

[1]P. Claus, W. Vycudilik, and W. Reider, Monatsh. Chem., 102, 1571 (1971).

EXAMPLE 6

Preparation of 4-carboethoxy-2-(thiomethoxymethyl) aniline from chlorodimethylsulfonium chloride and benzocaine.

Chlorodimethylsulfonium chloride complex was prepared as described in Example 5 for the preparation of 4-nitro-2-(thiomethoxymethyl)aniline. A solution of 3.30 g (0.02 mole) of benzocaine and 2.80 ml (0.02 mole) of triethylamine in 10 ml of dry methylene chloride was added dropwise to the clear solution of chlorodimethylsulfonium chloride to form the azasulfonium chloride salt of benzocaine. A voluminous white precipitate of the azasulfonium chloride salt formed and this was stirred for 6½ hours. At this time, 8.40 ml (0.06 mole) of triethylamine was added to the reaction mixture, the cooling bath was removed, and the solution stirred overnight. A work-up procedure substantially identical to that used in Example 5 for the preparation of 4-nitro-2-(thiomethoxymethyl) aniline gave a dark red oil which solidified upon standing. This oil was taken up in 100 ml of acetonitrile containing 5 ml of triethylamine and refluxed for 48 hours; the solvents were removed in vacuo to leave a red solid. Recrystallization from absolute ethanol gave 1.60 g (0.0071 mole), mp 83°–84° (analytical sample previously prepared mp 84.5°–85.5°), 35% yield of 4-carboethoxy-2-(thiomethoxymethyl)aniline. The ir and nmr spectra were identical to previously prepared samples.

EXAMPLE 7

Preparation of 2-(thiomethoxymethyl)aniline from bromodimethylsulfonium bromide and aniline.

A solution of 3.20 g (0.02 mole) of bromine in 100 ml dry methylene chloride was cooled to −78° (dry ice-acetone) under a static nitrogen pressure. To this dark red solution was added 1.55 ml (0.02 mole) of dimethyl sulfide in 10 ml of methylene chloride, a yellow precipitate formed immediately (NOTE: the yellow color persists even if another equivalent of dimethyl sulfide is added); the resultant solution containing the bromodimethylsulfonium bromide was stirred for 30 minutes. A solution of 1.86 g (0.02 mole) of aniline and 2.80 ml (0.02 mole) of triethylamine in 10 ml of dry methylene chloride was added dropwise to this bromodimethylsulfonium bromide solution, while maintaining the exotherm to less than 5° to form the azasulfonium salt of aniline. At the end of the addition the reaction was clear with no red color. The solution was stirred for 6 hours and no precipitate was observed. A solution of 3.24 g (0.06 mole) of sodium methoxide and 15 ml of absolute methanol was added, the cooling bath was allowed to warm to room temperature, and the reaction was stirred overnight (ca. 16 hr.). The reaction was quenched with 100 ml of 10% aqueous sodium hydroxide; the layers were separated; the aqueous phase was washed with two 100-ml portions of methylene chloride. The organic phases were combined, dried with anhydrous magnesium sulfate, filtered, and concentrated in vacuo to yield a yellow oil. This oil was taken up in 100 ml of acetonitrile containing 5 ml of triethylamine and refluxed for 5 hours. The solvent was removed in vacuo; the resultant oil was chromatographed on silica gel (etherhexane eluant) to produce 2.10 g (0.0137 mole), bp 88°–90° (0.12 mm), 69%, $n_D^{24.8}$ 1.6093 (lit[1] $n_D$ 1.6042 vs a previously prepared sample $n_D^{24.0}$ 1.6083) of 2-(thiomethoxymethyl)aniline. The ir and nmr spectra were identical to previously prepared samples.

[1]P. Claus, W. Vycudilik, and W. Reider, Monatsh. Chem., 102, 1571 (1971).

EXAMPLE 8

Preparation of 2-(2-tetrahydrothienyl)aniline from 1-chlorotetramethylenesulfonium chloride and aniline.

1-Chlorotetramethylenesulfonium chloride was prepared from chlorine and tetrahydrothiophene in a procedure identical to that used in Example 1 in the preparation of chlorodimethylsulfonium chloride. 2-(2-tetrahydrothienyl)-aniline was prepared from aniline and the 1-chlorotetramethylenesulfonium chloride through the azasulfonium halide salt followed by base treatment in 20% yield, in a procedure identical to that used in Example 2 for the preparation of 2-(thiomethoxymethyl)aniline from chlorodimethylsulfonium chloride and aniline except that the acetonitriletriethylamine reflux time was overnight (ca. 16 hr.), after column chromatography on silica gel (ether-hexane eluant) and distillation (bp 102°–105° (0.08 mm), $n_D^{22.2}$ 1.6251 (anal. sample previously prepared $n_D^{26.8}$ 1.6258). The ir and nmr spectra were identical to previously prepared samples

EXAMPLE 9

Preparation of 2-(2-tetrahydrothienyl)aniline from 1-bromotetramethylenesulfonium bromide and aniline.

1-Bromotetramethylenesulfonium bromide was prepared in a procedure identical to that used in Example 7 in the preparation of bromodimethylsulfonium bromide. 2-(2-tetrahydrothienyl)aniline was prepared from aniline and the 1-bromotetramethylenesulfonium bromide through the azasulfonium bromide salt followed by base treatment, in 19% yield, in a procedure identical to that used in Example 7 in the preparation of 2-(thiomethoxymethyl)aniline from bromodimethylsulfonium bromide and aniline except that the acetonitriletriethylamine reflux time was overnight (ca. 16 hr.).

EXAMPLES 10 to 13

General Procedure for the Synthesis of Indoles from Anilines and a Chlorine-sulfide Complex.

To a mechanically stirred solution of 2.0 ml (0.044 mol) of chlorine in 100 ml of methylene chloride, cooled to −70°, was added dropwise over a 20 minute period 4.6 g (0.044 mol) of methylthio-2-propanone dissolved in 15 ml of methylene chloride, while maintaining the temperature below −60°. The yellow solution decolorized and the chlorine:methylthio-2-propanone complex precipitated. Stirring of the mixture containing the complex was continued for 5 minutes and then 2 eq. (0.088 mol) of the aniline dissolved in 30 ml of methylene chloride was added to the mixture over a 30–60 minute period, while maintaining the temperature below −60° to form the azasulfonium salt. After another 30 minutes at −70°, 10 ml (0.069 mol) of triethylamine was added neat. The mixture was stirred for another 15 minutes at −70° and the cooling bath was removed. A clear solution resulted at room temperature, to which 50 ml of water was added to remove the amine hydrochloride. After separation of the layers, the organic solution was dried over anhydrous magnesium sulfate, filtered and evaporated to dryness. The indole derivative was isolated by column chromatography of the residue.

EXAMPLE 10

5-Methoxy-2-methyl-3-methylthioindole from Chlorine: Methylthio-2-Propanone Complex and 4-methoxyaniline (p-anisidine).

5-Methoxy-2-methyl-3-methylthioindole was synthesized from the complex and 4-methoxy via the azasulfonium halide salt following the above procedure. Column chromatography (silica gel and a 2:5 petroleum-ether/methylene chloride mixture) gave 3.44 g (0.017 mol, 38%) of the indole: mp 109°–111° (recr. from cyclohexane); ir (KBr) 3350 cm$^{-1}$ (NH); pmr (CCl$_4$) $\tau$2.17 (1H, br s, NH), 2.91 (1H, br s, 4-aryl H), 3.00 (1H, d, J = 8.0, 7-aryl H), 8.27 (1H, dd, J = 8.0 and 2.0 Hz, 6-aryl H), 6.18 (3H, s, OCH$_3$), 7.60 and 7.81 (3H each, s, SCH$_3$ and CH$_3$).

Anal. Calcd for C$_{11}$H$_{13}$NOS: C, 63.74; H, 6.32; N, 6.76; S, 15.47.

Found: C, 63.61; H, 6.30; N, 6.64; S, 15.41.

Desulfurization of 5-methoxy-2-methyl-3-methylthioindole (1.4 g, 6.75 mmol) with Raney nickel gave 5-methoxy-2-methylindole in a 72% yield, mp. 55°–56.5°. This solid was melted, cooled to −70° and slowly allowed to warm to room temperature. In this way a solid 5-methoxy-2-methyl-indole was obtained melting at 82°–84.5°, which corresponded well to the melting point reported in the literature (mp. 85°–86°).*

*E. Spath and O. Brunner, Ber., 58, 520 (1925).

EXAMPLE 11

2-Methyl-3-methylthioindole from Chlorine:methylthio-2-Propanone complex and Aniline.

2-Methyl-3-methylthioindole was synthesized from the complex and aniline via the azasulfonium chloride salt following the above procedure. Column chromatography (silica gel and a 1:2 petroleum-ether/methylene chloride mixture) of the residual mixture gave 5.28 g (0.030 mol, 68%) of 2-methyl-3-methylthioindole as a viscous oil, that solidified on standing to a material melting at 56.5°–58.3°. (A formerly prepared analytical sample had mp. 58°–59°. The N-chloroaniline route gave a 69% yield).

EXAMPLE 12

5-Chloro-2-methyl-3-methylthioindole from Chlorine: Methylthio-2-Propanone Complex and 4-chloroaniline.

5-Chloro-2-methyl-3-methylthioindole was synthesized from the complex and 4-chloroaniline following the above procedure. To complete the formation of the azasulfonium salt from the complex and 4-chloroaniline the mixture was stirred for 3 hours at −70° after the 4-chloroaniline solution had been added and before the triethylamine was added. Further work-up and column chromatography (silica gel and a 1:1 petroleum-ether/methylene chloride mixture) gave 4.14 g (0.020 mol, 45%) of 5-chloro-2-methyl-3-methylthioindole, mp. 62°–63.5°. (An analytical sample had mp. 64°–65.5° and the yield using the N-chloroaniline route for this indole was 72%).

EXAMPLE 13

5-Carboethoxy-2-methyl-3-methylthioindole from Chlorine:methylthio-2-Propanone Complex and 4-Carboethoxyaniline (Benzocaine).

5-Carboethoxy-2-methyl-3-methylthioindole was synthesized from the complex and 4-carboethoxyaniline via the azasulfonium salt following essentially the above procedure. In this case a solvent mixture of 75 ml of methylene chloride and 75 ml of acetonitrile was used for the 2.0 ml of chlorine and the 4.6 g (0.044 mol) of methylthio-2-propanone to form the complex in solution. The 0.088 mol of 4-carboethoxyaniline was added to the solution of the complex in 50 ml of acetonitrile to increase its solubility at low temperature and to form the azasulfonium chloride salt. Before the triethylamine was added, the mixture was stirred for 4 hours at −70° to maximize the azasulfonium salt formation. After warming to ambient temperature, a 50-ml portion of water was added and the layers were separated. The organic layer was extracted thoroughly with 2N aqueous HCl (to remove all of the unreacted aniline) and subsequently treated with saturated sodium bicarbonate. Drying of the organic solution over anhydrous magnesium sulfate followed by filtration and evaporation of the solvent gave a residue that was subjected to column chromatography (silica gel and methylene chloride). There was obtained 3.82 g (0.015 mol, 35%) of 5-carboethoxy-2-methyl-3-methylthioindole, mp 127°–130°. (An analytical sample had mp 126°–127°, and the yield using the N-chloroaniline route was 58%).

EXAMPLES 14 to 17

A General Procedure for the Synthesis of Oxindoles from Anilines and a Chlorine-Sulfide Complex.

To a mechanically stirred solution of 2.0 ml (0.044 mol) of chlorine in 100 ml of methylene chloride, cooled to −70°, was added dropwise over a 15 minute period 5.9 g (0.044 mol) of ethyl methylthioacetate dissolved in 15 ml of methylene chloride, while maintaining the temperature below −60°. The yellow solution of the chlorine:ethyl methylthioacetate complex decolorized. After 5 minutes a solution of 2 equivalents (0.088 mol) of the aniline dissolved in 30 ml of methylene chloride was added to the solution of the complex over a ca. 30 minute period, while maintaining the temperature below −60° to form the azasulfonium halide salt. Usually, a precipitate was formed at this stage.

Subsequently, the azasulfonium halide salt mixture was stirred for another hour at −70°, after which 10 ml (0.069 mol) of triethylamine was added neat. After another 30 minutes, the cooling bath was removed to allow warming to room temperature at which time a clear solution resulted. A 50-mol portion of water was added to remove the amine hydrochloride salt and the layers were separated. The organic solution was dried over anhydrous magnesium sulfate, filtered, and evaporated to dryness. The residue was redissolved in 150 ml of ether and stirred overnight with 20 ml of 2N aqueous HCl. Usually, the oxindole had precipitated and could be collected by filtration. In case no precipitate was formed, the two layers were separated and the ethereal solution was concentrated causing the oxindole to crystallize. This latter procedure also allowed the isolation of a second fraction in those cases where initially the oxindole had precipitated.

EXAMPLE 14

5-Methoxy-3-methylthio-2-oxindole from Chlorine:ethyl methylthioacetate Complex and 4-methoxyaniline.

5Methoxy-3-methylthio-2-oxindole was synthesized from the complex and 4-methoxyaniline via the above azasulfonium halide procedure. This allowed the isolation of 6.16 g of crude 5-methoxy-3-methylthio-2-oxindole that was recrystallized from methanol giving 4.90 g (0.023 mol, 53%) of pure 5-methoxy-3-methylthio-2-oxindole: mp 149°–150.5° (recr. from methanol); ir (KBr) 3400 and 3100 (NH), 1670 cm$^{-1}$ (c = 0); pmr (DMSO-d$_6$) τ−0.34 (1H, br s, NH), 3.00–3.22 (3H, m, aryl H), 5.50 (1H, s, CH), 6.26 (3H, s, OCH$_3$) and 8.00 (3H, s, SCH$_3$).

Anal. Calcd for C$_{10}$H$_{11}$NO$_2$S: C, 57.40; H, 5.30; N, 6.69; S, 15.32.

Found: C, 57.28; H, 5.36; N, 6.71; S, 15.20.

Desulfurization of 1.5 g (7.17 mmol) of 5-methoxy-3-methylthio-2-oxindole dissolved in 100 ml of absolute ethanol with W-2 Raney-Ni gave in 71% yield 5-methoxy-2-oxindole, mp. 148.5°–150.5° (lit. mp. 152°–154°).*

*C. F. Koelsch, J. Amer. Chem. Soc., 66, 2019 (1944).

EXAMPLE 15

3-Methylthio-2-oxindole from Chlorine:ethyl methylthioacetate Complex and Aniline.

3-Methylthio-2-oxindole was synthesized from the complex and aniline via the above azasulfonium halide salt and base treatment procedure. In this case the ethereal solution, containing the oxindole, was worked up by extracting it twice with 2N aqueous HCl, drying it over anhydrous magnesium sulfate followed by filtration and evaporation. The solid residue was dissolved in 30 ml of refluxing ethanol, which was poured into 125 ml of hot water. On standing, 5.10 g (0.029 mol, 65%) 3-methylthio-2-oxindole (mp 126°–127°, crystallized), which was collected by filtration. (An analytical sample melted at 126°–127°. The yield of 3-methylthio-2-oxindole via the N-chloroaniline route was 63%).

EXAMPLE 16

7-Methyl-3-methylthio-2-oxindole from Chlorine:ethyl Methylthioacetate Complex and 2-Methylaniline.

7-Methyl-3-methylthio-2-oxindole was synthesized from the complex and 2-methylaniline via the above azasulfonium salt and base treatment procedure. There was obtained 5.30 g (0.028 mol, 62%) of oxindole melting at 190.5°–193°. (An analytical sample melted at 194°–195.5°. The yield of 7-methyl-3-methylthio-2-oxindole via the N-chloroaniline route was 67%).

EXAMPLE 17

3-Methylthio-5-nitro-2-oxindole from Chlorine:ethyl methylthioacetate Complex and 4-Nitroaniline.

3-Methylthio-5-nitro-2-oxindole was synthesized from the complex and 4-nitroaniline via essentially the above azasulfonium salt and base treatment procedure with the following modifications. A mechanically stirred solution of 0.044 mol of the chlorine-sulfide complex was prepared in the usual manner in 420 ml of methylene chloride. Through an addition funnel, was added, as fast as possible, a solution of 13.1 g (0.088 mol) of 4-nitroaniline in 200 ml of methylene chloride containing 25 ml of acetonitrile to prevent premature crystallization of the nitro azasulfonium salt compound but causing a temperature rise to −40°. The mixture was stirred for an additional 5 hours at −70° before the triethylamine was added. After warming to room temperature, a 200-ml portion of water was added and the layers were separated. Cyclization to the oxindole was effected as described above, aafter which the layers were separated and the organic layer was extracted thoroughly with 2N aqueous HCl. After treatment with saturated sodium bicarbonate solution the organic extract was dried over anhydrous magnesium sulfate, filtered and concentrated, promoting the crystallization of the product. There was obtained 1.15 g (0.5 mmol, 12%) of 3-methylthio-5-nitro-2-oxindole, mp. 190°–193.5°. (An analytical sample melted at 196°–197°. The N-chloroaniline route gave a 51% yield).

We claim:

1. Process for preparing an azasulfonium halide salt which comprises
   a. reacting halogen with an organic sulfide compound having a formula selected from the group consisting of

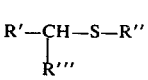   I wherein
   R' is hydrogen, lower alkyl or phenyl;
   R'', taken separately is lower alkyl or phenyl;
   R''', taken separately, is hydrogen, lower alkyl or phenyl; and
   R'' and R''', when taken together with the

moiety denote a ring containing 3 to 5 methylene carbon atoms;

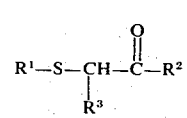   II(a)

and

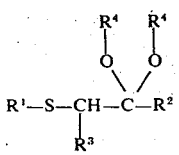 II(b)

wherein
R¹ is lower alkyl or phenyl;
R² is hydrogen, lower alkyl or phenyl;
R³ is hydrogen, lower alkyl; phenyl or benzyl R² can be attached to R³ as part of a cyclic ring system containing 5 to 8 carbon atoms;
each R⁴ is lower alkyl or the two R⁴ radicals are taken together with the —O—C—O— moiety to complete a cyclic ketal or acetal having from 3 to 4 carbon atoms in the ring;

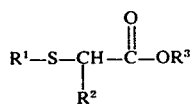 III(a)

and

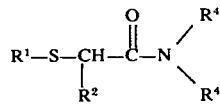 III(b)

wherein
R¹ is lower alkyl, phenyl or benzyl;
R² is hydrogen, lower alkyl, phenyl or benzyl;
R³ is lower alkyl, phenyl or benzyl;
each R⁴ is hydrogen or lower alkyl, or the two R⁴ groups are taken together with the nitrogen to form a ring containing from 4 to 5 methylene carbon atoms and up to one ring oxygen atom; to form a halogen:sulfur compound complex;
(b) reacting the halogen:sulfur compound complex from step (a) with an aniline or aminopyridine to form the azasulfonium halide aniline derivative.

2. Process of claim 1 wherein in step (a) the organic sulfide compound is a non-carbonylic di-hydrocarbon sulfide compound of the formula

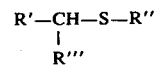 I wherein
R' is hydrogen, lower-alkyl or phenyl;
R", taken separately, is lower-alkyl or phenyl;
R'", taken separately, is hydrogen, lower-alkyl or phenyl; and
R" and R'" when taken together with the

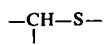

moiety denote a ring containing 3 to 5 methylene carbon atoms.

3. Process of claim 1 wherein in step (a) chlorine is reacted with a di-lower alkyl sulfide to form a chloro-di(lower alkyl)sulfonium chloride complex.

4. Process of claim 3 wherein in step (a) chlorine is reacted with dimethyl sulfide to form a chlorodimethylsulfonium chloride complex.

5. Process of claim 1 wherein in step (a) bromine is reacted with a di-lower alkyl sulfide to form a bromo-di-(loweralkyl)sulfonium bromide complex.

6. Process of claim 5 wherein in step (a) bromine is reacted with dimethylsulfide to form a bromodimethylsulfonium bromide complex.

7. A process of claim 3 wherein the chloro-di-(lower alkyl)sulfonium chloride is reacted with an anisidine to form a di-(lower alkyl)azasulfonium chloride salt of the anisidine.

8. A process of claim 7 wherein chlorodimethylsulfonium chloride complex is reacted with p-anisidine to form a dimethylazasulfonium chloride salt of p-anisidine.

9. Process of claim 1 wherein in step (a) the organic sulfide compound is a beta-carbonyl sulfide or a ketal or acetal thereof having a formula selected from the group consisting of

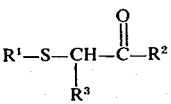 II(a)

and

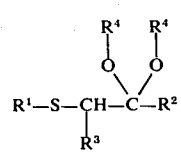 II(b)

wherein
R¹ is lower alkyl or phenyl;
R² is hydrogen, lower alkyl or phenyl;
R³ is hydrogen, lower alkyl, phenyl, or benzyl;
R² can be attached to R³ as part of a cyclic ring system containing 5 to 8 carbon atoms;
each R⁴ is lower alkyl or the two R⁴ radicals are taken together with the

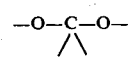

moiety to complete a cyclic ketal or acetal having from 3 to 4 carbon atoms in the ring.

10. Process of claim 9 wherein in step (a) chlorine is reacted with a beta-carbonyl sulfide of formula II(a) in claim 9 wherein R¹ is lower alkyl, R² is lower alkyl, and R³ is hydrogen to form a chlorine:beta-carbonyl sulfide complex.

11. Process of claim 10 wherein in step (a) chlorine is reacted with methylthio-2-propanone to form a chlorine:methylthio-2-propanone complex.

12. Process of claim 10 wherein the chlorine:beta-carbonyl sulfide complex is reacted with a methoxyaniline to form the azasulfonium salt of the methoxyaniline.

13. Process of claim 12 wherein a chlorine:methylthio-2-propanone complex is reacted with 4-methoxyaniline(anisidine) to form the azasulfonium salt of 4-methoxyaniline.

14. Process of claim 1 wherein in step (a) the organic sulfide compound is a beta-carboxylic ester or amide having a formula selected from the group consisting of

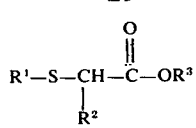

and

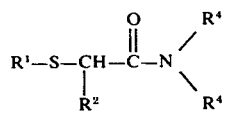

wherein
 R[1] is lower alkyl, phenyl or benzyl;
 R[2] is hydrogen, lower alkyl, phenyl, or benzyl;
 R[3] is lower alkyl, phenyl or benzyl;
 each R[4] is hydrogen or lower alkyl, or the two R[4] groups are taken together with the nitrogen to form a ring containing from 4 to 5 methylene carbon atoms and up to one ring oxygen atom.

15. Process of claim 14 wherein in step (a) chlorine is reacted with a beta-carboxylic ester of formula III(a) in claim 14 wherein R[1] is lower alkyl, R[2] is hydrogen and R[3] is lower alkyl to form a chlorine:beta-carboxylic ester complex.

16. Process of claim 15 wherein chlorine is reacted with ethyl methylthioacetate to form a chlorine:ethyl methylthioacetate complex.

17. Process of claim 15 wherein the chlorine:beta-carboxylic ester complex is reacted with a methoxyaniline to form the azasulfonium salt of the methoxyaniline.

18. Process of claim 17 wherein a chlorine:ethyl methylthioacetate complex is reacted with 4-methoxyaniline(anisidine) to form the azasulfonium chloride salt of 4-methoxyaniline.

19. The process of claim 1 wherein the aniline or aminopyridine has a free unsubstituted position on the aromatic ring ortho to the amino group and wherein the reaction is conducted under substantially anhydrous conditions in an organic liquid medium.

* * * * *

UNITED STATES PATENT OFFICE
CERTIFICATE OF CORRECTION

Patent No. 3,960,926          Dated June 1, 1976

Inventor(s) Paul G. Gassman; Gordon D. Gruetzmacher

It is certified that error appears in the above-identified patent and that said Letters Patent are hereby corrected as shown below:

Col. 2, line 63:   alakylated -- should read:   -- alkylated --.

Col. 7, line 19:   9°C. -- should read:   -- 0°C. --.

line 26:   teh -- should read: -- the --.

Col. 13, line 30:  4-methoxy -- should read: -- 4-methoxyaniline --

Col. 15, line 24:  5methoxy -- should read:  5-methoxy --.

Signed and Sealed this

Ninth Day of November 1976

[SEAL]

Attest:

RUTH C. MASON
Attesting Officer

C. MARSHALL DANN
Commissioner of Patents and Trademarks